United States Patent [19]
Hahnen et al.

[11] Patent Number: 5,902,300
[45] Date of Patent: May 11, 1999

[54] ELECTRODES HAVING UPPER AND LOWER OPERATING SURFACES FOR ELECTROCAUTERY PROBES FOR USE WITH A RESECTOSCOPE

[75] Inventors: Kevin F. Hahnen, Pleasanton, Calif.; Boris Kesler, Hialeah, Fla.

[73] Assignee: Symbiosis Corporation, Miami, Fla.

[21] Appl. No.: 08/794,998

[22] Filed: Feb. 5, 1997

[51] Int. Cl.$^6$ .................................................. A61B 17/39
[52] U.S. Cl. .................................................. 606/46; 606/49
[58] Field of Search .................................. 606/41, 45, 46, 606/49; 219/233

[56] References Cited

U.S. PATENT DOCUMENTS

| | | | |
|---|---|---|---|
| 1,930,214 | 10/1933 | Wappler | 174/89 |
| 1,932,258 | 10/1933 | Wappler | 606/49 |
| 1,963,636 | 6/1934 | Wappler | 174/89 |
| 1,971,024 | 8/1934 | Wappler | 174/89 |
| 1,995,725 | 3/1935 | Wappler | 606/45 |
| 2,002,594 | 5/1935 | Wappler et al. | 174/89 |
| 2,004,559 | 6/1935 | Wappler et al. | 174/89 |
| 2,011,169 | 8/1935 | Wappler | 174/89 |
| 2,090,923 | 8/1937 | Wappler | 128/303.15 |
| 2,101,913 | 12/1937 | Meyer | 219/233 |
| 2,224,464 | 12/1940 | Wolf | 128/303.14 |
| 2,484,059 | 10/1949 | Wallace | 606/46 |
| 2,487,502 | 11/1949 | Willinsky | 128/303.14 |
| 2,815,757 | 12/1957 | Piar | 128/303.14 |
| 3,149,633 | 9/1964 | Zingale | 128/303.15 |
| 3,752,159 | 8/1973 | Wappler | 128/303.15 |
| 3,856,015 | 12/1974 | Iglesias | 128/303.15 |
| 3,881,087 | 4/1975 | Nicosia | 219/233 |
| 3,939,839 | 2/1976 | Curtiss | 128/303.15 |
| 3,973,568 | 8/1976 | Iglesias | 128/303.15 |
| 3,990,456 | 11/1976 | Iglesias | 128/303.15 |
| 4,030,502 | 6/1977 | Iglesias | 128/303.15 |
| 4,134,406 | 1/1979 | Iglesias | 128/303.15 |
| 4,149,538 | 4/1979 | Mrava et al. | 128/303.15 |
| 4,362,160 | 12/1982 | Hiltebrandt | 128/303.15 |
| 4,506,668 | 3/1985 | König | 128/303.15 |
| 4,649,917 | 3/1987 | Karasawa | 128/303.14 |
| 4,657,018 | 4/1987 | Hakky | 128/303.15 |
| 4,726,370 | 2/1988 | Karasawa et al. | 128/303.15 |
| 4,917,082 | 4/1990 | Grossi et al. | 606/46 |
| 5,007,907 | 4/1991 | Nishigaki et al. | 606/46 |
| 5,047,027 | 9/1991 | Rydell | 606/48 |
| 5,064,424 | 11/1991 | Bitrolf | 606/46 |
| 5,088,998 | 2/1992 | Sakashita et al. | 606/46 |
| 5,196,011 | 3/1993 | Korth et al. | 606/46 |

(List continued on next page.)

FOREIGN PATENT DOCUMENTS

| | | | |
|---|---|---|---|
| 3707-403 | 9/1987 | Germany | 606/46 |
| 26880 | of 1905 | United Kingdom . | |

OTHER PUBLICATIONS

Gorsch, "Biopsy in Proctology," American Journal of Surgery, p. 484. (copy 606/45) Jun. 1936.

*Primary Examiner*—Lee Cohen
*Attorney, Agent, or Firm*—Testa, Hurwitz & Thibeault, LLP

[57] ABSTRACT

Electrodes for electrocautery probes for use with a resectoscope include full loop electrodes wherein the full loop has a working surface which extends below the axis of the cautery probe and a working surface which extends above the axis of the cautery probe, composite full loop electrodes wherein the upper working surface and the lower working surface have different morphology, combined full loop and roller electrodes wherein one of the upper or lower portions of the loop serves as the axle for a roller electrode, and bifurcated full loop electrodes wherein the upper working surface and the lower working surface can be independently energized. The electrodes according to the invention permit resection of upper and lower prostate lobes without requiring inversion of the resectoscope, thereby shortening the time for the procedure. In addition, the full loop electrodes with different upper and lower morphology provide additional treatment options while also reducing the time for the procedure. Furthermore, the bifurcated full loop electrodes provide the ability to use different power settings for the upper and lower working surfaces.

4 Claims, 4 Drawing Sheets

U.S. PATENT DOCUMENTS

| | | | |
|---|---|---|---|
| 5,201,741 | 4/1993 | Dulebohn | 606/113 |
| 5,261,906 | 11/1993 | Pennino et al. | 606/46 |
| 5,318,564 | 6/1994 | Eggers | 606/47 |
| 5,324,288 | 6/1994 | Billings et al. | 606/45 |
| 5,342,357 | 8/1994 | Nardella | 606/40 |
| 5,354,296 | 10/1994 | Turkel | 606/41 |
| 5,374,188 | 12/1994 | Frank et al. | 433/32 |
| 5,376,087 | 12/1994 | Haber et al. | 606/27 |
| 5,395,312 | 3/1995 | Desai | 604/22 |
| 5,395,363 | 3/1995 | Billings et al. | 606/41 |
| 5,395,368 | 3/1995 | Ellman et al. | 606/45 |
| 5,582,610 | 12/1996 | Grossi et al. | 606/46 |
| 5,599,349 | 2/1997 | D'Amelio | 606/46 |
| 5,634,924 | 6/1997 | Turkel et al. | 606/46 |

ELECTRODES HAVING UPPER AND LOWER OPERATING SURFACES FOR ELECTROCAUTERY PROBES FOR USE WITH A RESECTOSCOPE

This application is a related to application Ser. No. 08/795,000, filed Feb 05, 1997, and application Ser. No. 08/425,386, filed Apr. 20, 1995, now U.S. Pat. No. 5,569,244, the complete disclosures of which are hereby incorporated by reference herein in their entireties.

BACKGROUND OF THE INVENTION

1. Field of the Invention

This invention relates broadly to endoscopic instruments. More particularly, this invention relates to electrodes which are used in electrocautery probes with a resectoscope.

2. State of the Art

Electrosurgical resection is a procedure in which damaged or enlarged tissue is excised with an electrocautery probe. Transurethral resection is an electrosurgical procedure in which a portion of the prostate is excised by means of an instrument passed through the urethra. Endometrial ablation is an electrosurgical alternative procedure to hysterectomy for women with menorrhagia (abnormal or excessive uterine bleeding). In both procedures, the instrument typically used is called a resectoscope or hysteroscope. Prior art FIG. 1 shows a typical resectoscope 10 with an electrocautery probe 12. The resectoscope 10 includes a distal guide tube 14 and a proximal handle 16. A telescope 18 is inserted through the guide tube 14 and is provided with a proximal eye piece 20 for viewing the interior of the bladder or other operative site. The cautery probe 12 has a distal electrode 22 which is mounted between a pair of arms 23, 25. The arms 23, 25 are joined at their proximal ends to an electrode lead 27 which is coupled via the handle 16 to a wire 24 which is coupled to a source of cautery current (not shown). A mounting sleeve 29 is provided on the probe 12 for slideably coupling it to the guide tube 14. The mounting sleeve 29 is typically located at the point where the arms 23, 25 are joined to the electrode lead 27. The handle 16 is generally capable of axially sliding the probe 12 and its distally mounted electrode 22 relative to the guide tube 14.

The resection procedure involves applying a cauterizing voltage to the electrode 22 and moving the electrode slowly through or over the prostate or endometrium while viewing the tissue through the scope 18. Thermal energy (in the form of an electrical signal) is applied through the electrode to the prostate or the endometrium so that tissue is excised. The resectoscope and cautery probe are also useful in other procedures for resecting the uterus, ureter, or renal pelvis.

Known electrodes for use in resectoscopes are available in many different shapes and sizes. U.S. Pat. No. 4,917,082 to Grossi et al., for example, discloses several embodiments of a "Resectoscope Electrode" including a coagulating electrode, a knife electrode, a punctate electrode, and a roller electrode, among others. Electrodes for use with resectoscopes are also widely available from Olsen Electrosurgical, Inc., Concord, Calif. They are available as blades, needles, balls, loops, spear tips, flexible wires, semi-circular wires, hooks, spatulas and blunt tips.

Most of the known electrodes extend downward from a pair of probe arms and present a single working surface which is located below the axis of the probe arms and below the axis of the scope. Thus, in order to operate on tissue which is located above the probe arms, the entire resectoscope must be rotated 180° to bring the working surface of the electrode in contact with the tissue. U.S. Pat. No. 5,007,907 to Nishigaki et al. and U.S. Pat. No. 5,196,011 to Korth et al. disclose electrodes which are suspended from a single probe arm. Nishigaki et al. discloses a special probe arm which is located above the scope and which has a loop which extends below the axis of the probe arm. Korth et al. discloses an electrode in the shape of a triangle which is suspended at its vertex from a single probe arm. While these patents would appear to show "full loop" electrodes, the electrodes shown do not have upper and lower working surfaces.

SUMMARY OF THE INVENTION

It is therefore an object of the invention to provide an electrode having upper and lower operating surfaces for use in an electrocautery probe with a resectoscope.

It is also an object of the invention to provide an electrode having upper and lower operating surfaces of different morphology for use in an electrocautery probe with a resectoscope.

It is another object of the invention to provide an electrode having upper and lower operating surfaces which can be separately energized for use in an electrocautery probe with a resectoscope.

In accord with these objects which will be discussed in detail below, the electrodes of the present invention include full loop electrodes wherein the full loop has a working surface which extends below the axis of the cautery probe and a working surface which extends above the axis of the cautery probe, composite full loop electrodes wherein the upper working surface and the lower working surface have different morphology, combined full loop and roller electrodes wherein one of the upper or lower portions of the loop serves as the axle for a roller electrode, and bifurcated full loop electrodes wherein the upper working surface and the lower working surface can be independently energized.

The electrodes according to the invention permit resection of upper and lower prostate lobes without requiring inversion of the resectoscope, thereby shortening the time for the procedure. In addition, the full loop electrodes with different upper and lower morphologies provide additional treatment options while also reducing the time for the procedure. Furthermore, the bifurcated full loop electrodes provide the ability to use different power settings for the upper and lower working surfaces. Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
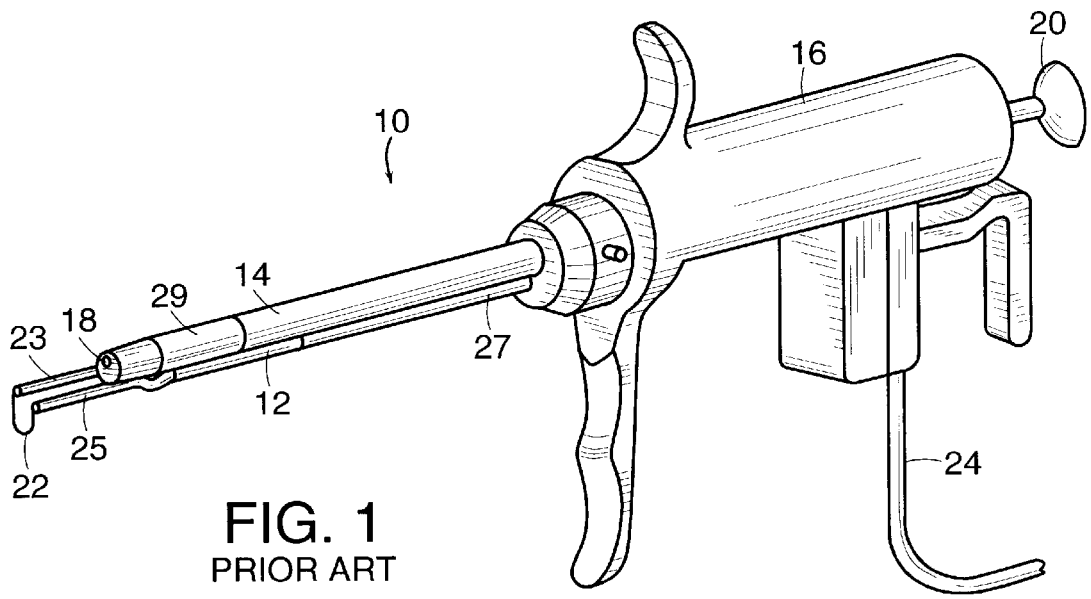
FIG. 1 is a perspective view of a prior art resectoscope with an electrocautery probe having a loop electrode.
Figure 2:
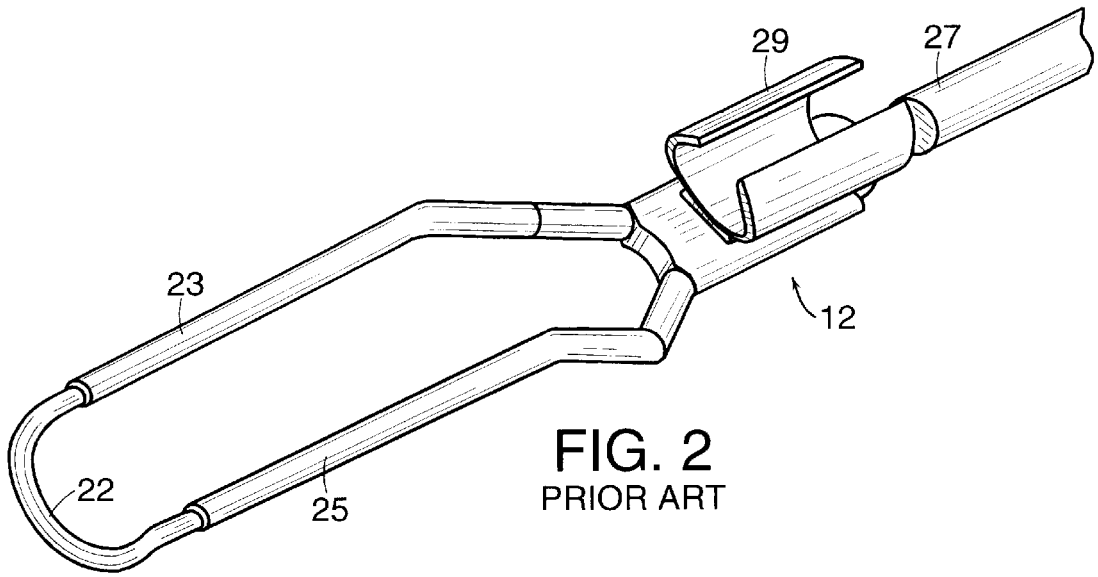
FIG. 2 is an enlarged broken perspective view of the prior art electrocautery probe of FIG. 1.
Figure 3:
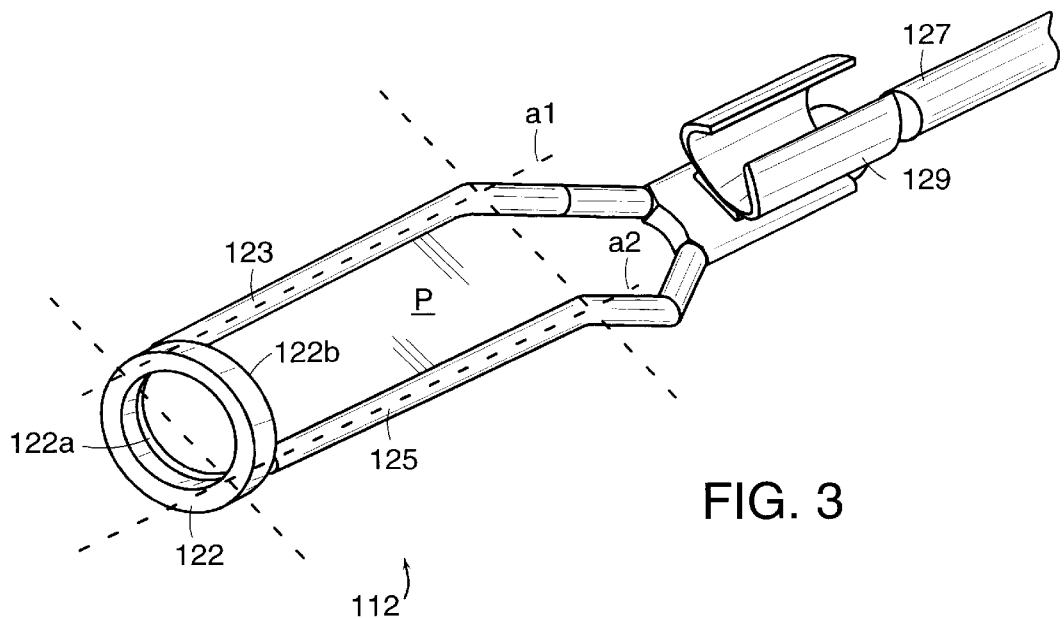
FIG. 3 is an enlarged broken perspective view of the distal end of an electrocautery probe incorporating a first embodiment of a full loop electrode according to the invention.

Referring now to FIG. 3, a cautery probe 112 according to the invention has a full loop or circular electrode 122 which is mounted between a pair of insulated arms 123, 125 such that substantially half of the electrode extends above a plane P defined by the axes a1, a2 of the arms and substantially half of the electrode extends below the plane. The arms 123, 125 are joined at their proximal ends to an electrode lead 127 and a resectoscope mounting sleeve 129 is provided preferably at the location where the arms 123, 125 are joined to the electrode lead 127. The electrode 122 according to the invention is preferably made from a single piece of superalloy, stainless steel, tungsten, or copper which is soldered or welded to the distal ends of the arms 123, 125. An exemplary embodiment of the electrode is approximately 0.20 inches in diameter and fits into a STORZ Resectoscope using a 27 FR cannula. As will be described in more detail below, the exact morphology of the full loop electrode may be varied considerably according to the invention. The common feature of all of the embodiments of the invention is that the electrode 122 has a lower working surface 122a and an upper working surface 122b. Moreover, the structure of the probe upon which the electrode is mounted may also be varied in several ways. For example, an alternative first embodiment of the invention utilizing a different type of probe is shown in FIG. 4.

Figure 4:
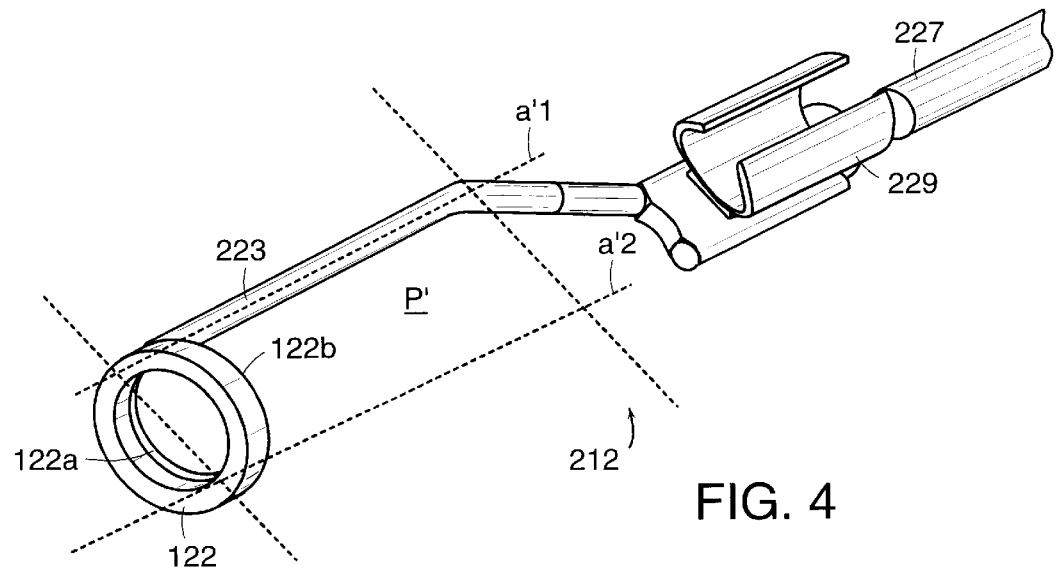
FIG. 4 is a view similar to FIG. 3 of an alternate first embodiment of a full loop electrode according to the invention.

Referring now to FIG. 4, a cautery probe 212 according to the invention has a full loop electrode 122 which is identical to the electrode described above. The difference between this embodiment and the embodiment described above is that the probe 212 has only one arm 223. The single arm 223 is configured in the same manner as the arm 123 described above and is coupled to an electrode lead 227 and a resectoscope mounting sleeve 229. This alternate embodiment combines the features of the present invention with features disclosed in the above-referenced related application [SYM-273]. In this embodiment, the lower working surface 122a and the upper working surface 122b of the electrode 122 extend below and above an imaginary plane P' which includes the axis a'1 of the single probe arm 223 and the imaginary axis a'2 of the missing probe arm.

As mentioned above, the morphology of the full loop electrodes according to the invention may be varied considerably. The electrode may have a conventional cylindrical wire profile, a broad band ribbon profile, a wedge profile, or a knife profile. Moreover, the full loop may have a composite of two or more profiles. Exemplary composite full loop electrodes are shown in FIGS. 5 through 7.

Figure 5:
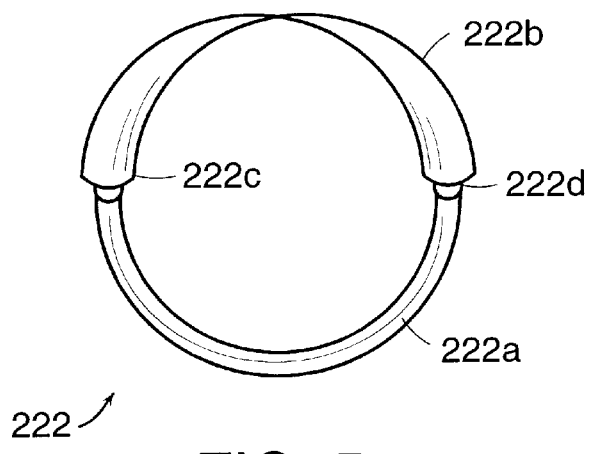
FIG. 5 is an enlarged perspective view of a second embodiment of a full loop electrode according to the invention wherein the upper working surface and the lower working surface have different morphologies.

Turning now to FIG. 5, a composite full loop electrode 222 according to the invention has a lower portion 222a with a cylindrical wire profile and an upper portion 222b with a broad band ribbon profile. The lower portion of the electrode is useful for cutting and the upper portion is useful for coagulating. The electrode 222 may be formed from a single piece of metal or may be formed from two pieces which are soldered or welded together at the points 222c, 222d. As shown, each portion 222a, 222b of the electrode 222 occupies approximately 180° of the full loop. However, the upper and lower portions of the electrode need not occupy the same angular length. The electrode 222 is coupled to the arms of a cautery probe in the same manner as the electrode 122 described above.

Figure 6:
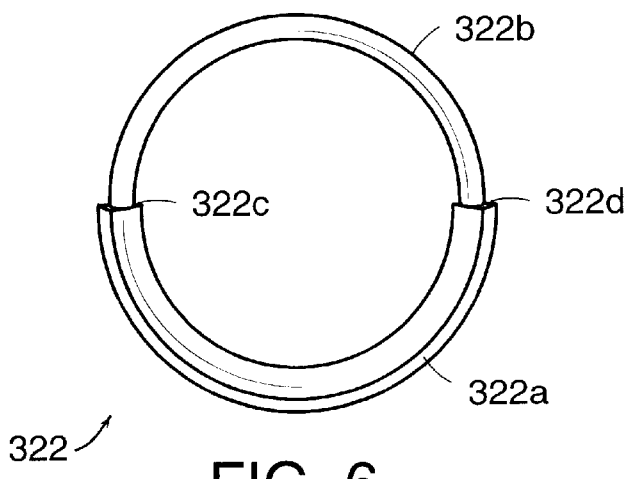
FIG. 6 is an enlarged perspective view of a third embodiment of a full loop electrode according to the invention wherein the upper working surface and the lower working surface have different morphologies.
Figure 7:
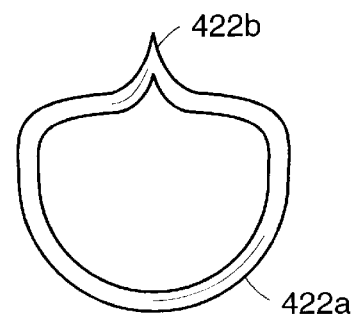
FIG. 7 is an enlarged end view of a fourth embodiment of a full loop electrode according to the invention wherein the upper working surface and the lower working surface have different morphologies.

Referring now to FIG. 6, a composite full loop electrode 322 according to the invention has a lower portion 322a with a wedge profile, such as that disclosed in previously incorporated application Ser. No. 08/425,386, and an upper portion 322b with a cylindrical wire profile. The lower portion of the electrode is useful for simultaneous cutting and coagulating and the upper portion is useful for cutting. The electrode 322 may be formed from a single piece of metal or may be formed from two pieces which are soldered or welded together at the points 322c, 322d. As shown, each portion 322a, 322b of the electrode 322 occupies approximately 180° of the full loop. However, the upper and lower portions of the electrode need not occupy the same angular length. The electrode 322 is coupled to the arms of a cautery probe in the same manner as the electrode 122 described above.

From the foregoing, those skilled in the art will appreciate that the composite full loop electrodes according to the invention may incorporate many different morphologies. FIG. 7 shows yet another type of composite full loop electrode according to the invention. The electrode 422 shown in FIG. 7 has a lower loop 422a and an upper knife 422b. The electrode may be formed from a single piece of wire which is crimped to form the knife portion 422b of the electrode. The electrode 422 is coupled to the arms of a cautery probe in the same manner as the electrode 122 described above.

In addition to providing full loop electrodes with different upper and lower morphologies, the invention provides a combined loop and roller electrode wherein a portion of a full loop electrode serves as the axle for a roller. Such an electrode according to the invention is shown in FIG. 8.

Figure 8:
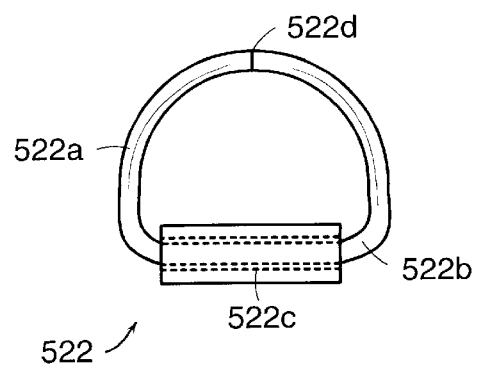
FIG. 8 is an enlarged end view of a fifth embodiment of a full loop electrode according to the invention wherein one of the upper or lower portions of the loop serves as the axle for a roller electrode.

Turning now to FIG. 8, a composite roller and loop electrode 522 according to the invention includes a wire full loop 522a with a straight portion 522b upon which a roller 522c is mounted. The electrode 522 is formed from a wire upon which the roller 522c is mounted and which is then bent and then soldered or welded at some point 522d in order to form a full loop. The electrode 522 is coupled to the arms of a cautery probe in the same manner as the electrode 122 described above.

From the foregoing, those skilled in the art will appreciate that the features of the electrodes shown in FIGS. 5 through 8 may be combined in different ways and that the upper and lower working surfaces may be reversed. For example, a composite full loop electrode according to the invention may have an upper roller with a lower knife, an upper wedge with a lower ribbon, etc.

Figure 9:
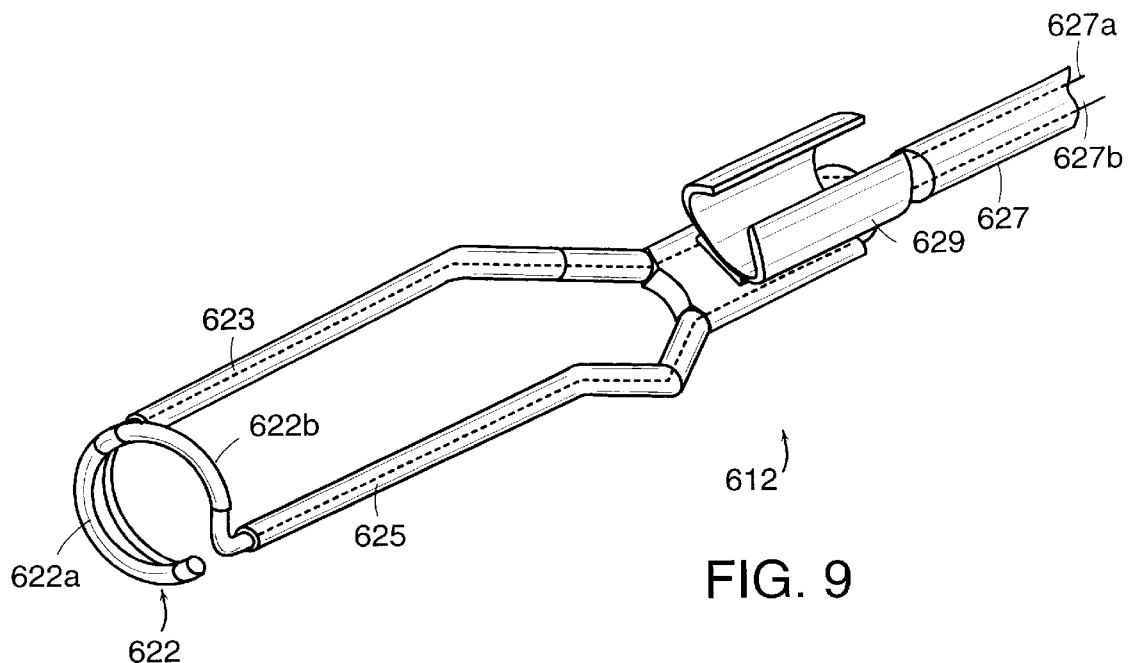
FIG. 9 is an enlarged broken perspective view of the distal end of an electrocautery probe incorporating a sixth embodiment of full loop electrode according to the invention wherein the upper working surface and the lower working surface can be independently energized.

According to another aspect of the invention, a full loop electrode is bifurcated so that upper and lower working surfaces may be energized independently. Referring now to FIG. 9, a cautery probe 612 according to the invention has a bifurcated full loop electrode 622 which is mounted between a pair of insulated arms 623, 625 such that substantially half of the electrode 622b extends above a plane defined by the axes of the arms and substantially half of the electrode 622a extends below the plane. The arms 623, 625 are mechanically joined at their proximal ends to an electrode lead stem 627 and a resectoscope mounting sleeve 629 is provided preferably at the location where the arms 623, 625 are joined to the electrode lead stem 627. As shown in FIG. 9, the lower portion 622a of the electrode 622 is electrically coupled to the arm 623 and the upper portion 622b of the electrode 622 is electrically coupled to the arm 625. Each arm is electrically coupled to a separate electrode lead 627a, 627b and the electrode leads are insulated from each other in the electrode lead stem. From the foregoing, it will be appreciated that the application of cautery current to the electrode lead 627a will energize the lower portion 622a of the electrode 622 and that the application of cautery current to the electrode lead 627b will energize the upper portion 622b of the electrode 622. It will further be appreciated that in order to take advantage of this cautery probe, a resectoscope may be modified to accommodate the two electrode leads 627a, 627b and to provide means for separately energizing the leads. While these modifications are not shown, those skilled in the art will understand how the resectoscope should be modified. The electrode 622 enables the practitioner to set separate current settings for the upper and lower portions of the electrode as well as to selectively energize the upper and lower portions individually. As shown in FIG. 9, the lower portion 622a and the upper portion 622b are physically separate pieces. However, it will be appreciated that these portions of the electrode 622 may be physically coupled to each other with any non-conductive material such as a ceramic. Such physical coupling of the upper and lower portions of the electrode can add stability to the entire electrode and facilitate manufacturing of probes incorporating such an electrode.

There have been described and illustrated herein several embodiments of electrodes having upper and lower operating surfaces. While particular embodiments of the invention have been described, it is not intended that the invention be limited thereto, as it is intended that the invention be as broad in scope as the art will allow and that the specification be read likewise. Thus, while particular dimensions have been disclosed, it will be appreciated that other dimensions could be utilized. Also, while curved electrodes have been shown, it will be recognized that polygonal electrodes could be used with similar results obtained. Moreover, while particular configurations have been disclosed in reference to welding and soldering, it will be appreciated that other configurations could be used as well. It will therefore be appreciated by those skilled in the art that yet other modifications could be made to the provided invention without deviating from its spirit and scope as so claimed.

We claim:

1. An electrocautery probe comprising:

at least one arm having a distal end and a longitudinal axis, and an electrode extending from the distal end, said electrode for receiving a cautery current and comprising a first portion extending above the longitudinal axis and a second portion extending below the longitudinal axis, said first and second portions forming a substantially circular loop, said first portion having a morphology chosen from the group consisting of a wire loop, a wedge, a ribbon, a knife, and a roller, and said second portion having a different morphology chosen from the group consisting of a wire loop, a wedge, a ribbon, a knife, and a roller.

2. An electrocautery probe according to claim 1, wherein said at least one arm comprises a first conductive arm having a proximal end, a distal end, and a first longitudinal axis, and a second conductive arm having a proximal end, a distal end, and a second longitudinal axis, said first and second longitudinal axes defining a plane, wherein said first portion extends above said plane and said second portion extends below said plane.

3. An electrocautery probe comprising:

at least one arm having a distal end and a longitudinal axis, and an electrode extending from the distal end, said electrode for receiving a cautery current and comprising a first portion extending above the longitudinal axis and a second portion extending below the longitudinal axis, said first and second portions forming a substantially circular loop and said first and second portions being electrically insulated from each other for being energized separately.

4. An electrocautery probe according to claim 3, wherein said at least one arm comprises a first conductive arm having a proximal end, a distal end, and a first longitudinal axis, and a second conductive arm having a proximal end, a distal end, and a second longitudinal axis, said first and second longitudinal axes defining a plane, wherein said first portion extends above said plane and said second portion extends below said plane.

* * * * *